(12) United States Patent
Vogt et al.

(10) Patent No.: US 9,101,699 B2
(45) Date of Patent: Aug. 11, 2015

(54) DEVICE FOR WETTING A MEDICAL EQUIPMENT COMPONENT

(75) Inventors: Juergen Vogt, Eiterfeld (DE); Eduard Fransen, Fulda (DE)

(73) Assignee: FRESENIUS KABI DEUTSCHLAND GMBH, Bad Homburg (DE)

( * ) Notice: Subject to any disclaimer, the term of this patent is extended or adjusted under 35 U.S.C. 154(b) by 51 days.

(21) Appl. No.: 13/421,913

(22) Filed: Mar. 16, 2012

(65) Prior Publication Data

US 2012/0273007 A1 Nov. 1, 2012

Related U.S. Application Data

(60) Provisional application No. 61/479,417, filed on Apr. 27, 2011.

(30) Foreign Application Priority Data

Apr. 27, 2011 (EP) ..................................... 11163835

(51) Int. Cl.
*B05C 7/00* (2006.01)
*A61M 5/00* (2006.01)
(52) U.S. Cl.
CPC ....................................... *A61M 5/00* (2013.01)
(58) Field of Classification Search
None
See application file for complete search history.

(56) References Cited

U.S. PATENT DOCUMENTS

| 3,661,621 | A | 5/1972 | Jager | |
|---|---|---|---|---|
| 4,512,947 | A | 4/1985 | Wyle et al. | |
| 5,683,541 | A | 11/1997 | Bocchi | |
| 5,871,584 | A | 2/1999 | Tateyama et al. | |
| 6,179,807 | B1 * | 1/2001 | Henniges et al. | ............... 604/35 |
| 6,458,094 | B1 * | 10/2002 | McMahon et al. | ............... 604/35 |

FOREIGN PATENT DOCUMENTS

DE 10231231 2/2004

* cited by examiner

*Primary Examiner* — Jason Ko
(74) *Attorney, Agent, or Firm* — Occhiuti & Rohlicek LLP (57) ABSTRACT

The invention concerns a device (1) for wetting a medical equipment component (20) with a liquid medium (M), having a dispenser (10) for applying the liquid medium (M) to a section (200) of the component (20) that is to be wetted. A device of this type is characterized by a suction device (12) for drawing off at least a portion of the liquid medium (M) from the section (200) of the component (20) that is to be wetted. The invention furthermore concerns a method for wetting a component. In this manner, a device and a method for wetting a component with a liquid medium is created, with which a wetting procedure can be executed in an at least partially automated manner, at least partially reducing the risk thereby of blockage at the opening of the component as a result of too much liquid being applied.

10 Claims, 4 Drawing Sheets

DEVICE FOR WETTING A MEDICAL EQUIPMENT COMPONENT

CROSS REFERENCE TO RELATED APPLICATIONS

This application is claims priority to U.S. Provisional Application No. 61/479,417 and European Application No. 11 163 835.9, both filed on Apr. 27, 2011. The aforementioned applications are incorporated by reference herein.

The invention concerns a device for wetting a medical equipment component with a liquid medium according to the preamble of Claim 1, and a method for wetting a component with a liquid medium.

A device of this type for wetting a medical equipment component with a liquid medium has a dispenser for applying the liquid medium to a section of the component that is to be wetted.

In this case, a medical equipment component relates to a component of a medical equipment apparatus that should be wetted in order for said component to be attached to another component in, for example, an adhesive manner. The medical equipment component can be designed, for example, as a (flexible) tube of an infusion set or a (rigid) plastic part of a medical equipment apparatus.

The liquid medium with which the medical equipment component is to be wetted, can be, for example, an adhesive that is to be applied to the component, by means of which said component is to be attached to another component in an adhesive manner. It is also conceivable that the liquid medium with which the component is to be wetted relates to another liquid, e.g. a lubricating agent, in particular isopropanol, for facilitating a connection between two components, or a medical silicone for siliconizing a component.

If, in the conventional manner, a medical equipment component in the form of a tube from an infusion set is to be connected in an adhesive manner with another component, e.g. a connector or a drip chamber of the infusion set, then one end of the tube is dipped into a petri dish containing a liquid medium, by means of which the tube can be connected to the connector or drip chamber in an adhesive manner.

This conventional wetting method for the application of the liquid medium to one end of a tube of this type is a difficult technical process.

Irregularities in the application of the liquid medium to the component that is to be wetted may arise, for example, because the component is not fully dipped with the end that is to be wetted, into the petri dish, thus resulting in an incomplete wetting of the section that is to be wetted (human factors may affect the outcome).

In addition, the level of the liquid in the petri dish decreases over time as a result of evaporation of the medium and as a result of depletion of the medium during the wetting process. Through irregular refilling of the liquid medium and the thereby resulting variable levels of the liquid in the petri dish, further irregularities in the wetting of the component may arise.

A further problem in the technical process with the prior wetting procedure results from the fact that in wetting an end of a tube by dipping said in a liquid medium—due to the capillary effect at the tube opening of the end of the tube—after removing the tube from the petri dish, some liquid remains in the tube opening that has been dipped, which can lead to blockage in the tube opening. This is to be prevented in the conventional approach in that the dipped end, after it has been removed, is to be swabbed out by mean of a so-called sponge disc, in order that residual liquid be removed from the tube opening. In this case, however, the problem arises that an insufficient removal of the liquid from the tube opening may occur if the swabbing with the sponge disc is not properly executed, or if the sponge disc is saturated with the liquid medium, such that it is unable to absorb any further liquid. In addition, contamination by particles found in the sponge disc may occur, which remain on the component as a result of the swabbing.

Furthermore, the conventional, entirely manually executed wetting procedure is limited in that with a dipping of a tube end having a tube opening in a liquid medium, it is a inevitable that both the interior and exterior walls of the tube opening of the dipped end are always wetted. A selective wetting of only the interior walls or only the exterior walls cannot be obtained by means of a simple dipping procedure.

Furthermore, due to evaporation of the liquid medium from the petri dish being used, a odor, disturbing for the user, may result.

Because a conventional wetting procedure of this type is executed in a purely manual fashion, it is comparatively slow, inefficient and furthermore, subject to error. Although, for example, through a constant monitoring of the level of the liquid in a petri dish that is being used, through careful swabbing with the sponge disc, through regular replacement of a saturated sponge disc and through ventilation in the workplace, a portion of the prior technical problems can be reliably overcome, a desire for an improved wetting procedure remains, with which, in particular, the human factors can be eliminated.

From U.S. Pat. No. 5,683,541 a device for cutting and wetting a plastic tube is known, with which a dispenser for applying a liquid medium to an end of a plastic tube is implemented. The plastic tube is placed with one end at the dispenser for wetting, and selectively, depending on the design of the dispenser, a tube opening is wetted on its interior or exterior walls.

With the device known from U.S. Pat. No. 5,683,541, it may also be the case that after wetting, too much of the liquid medium remains in or on the tube end that is to be wetted, such that in some cases this may result in a blockage of an opening of the tube.

The present invention has the objective of providing a device and a method for wetting a component with a liquid medium, with which a wetting procedure can at least in part be executed automatically, and thereby the risk of blockage to the opening of the component as a result of too much liquid being applied, is at least reduced.

This objective is achieved by means of the subject matter having the characteristics specified in Claim 1.

Accordingly, a suction device for removing at least a portion of the liquid medium from the section of the component that is to be wetted is provided with said device.

The present invention is based on the idea that by means of the dispenser, a liquid medium can be introduced to a section of a medical equipment component that is to be wetted, e.g. a plastic tube, and excess liquid can be removed by means of the suction device after said liquid has been applied, such that excess liquid does not remain on the component, and cannot result in a blockage to the opening of the component. In particular, in this manner a capillary effect on an opening of a component to be wetted can be counteracted, in that by means of the suction device, the liquid that has been introduced is removed, such that the risk of blockage in this component opening is substantially prevented.

The dispenser advantageously has at least one application fixture, to which the component can be applied along the application axis, and which at least in sections, extends along the application axis. For wetting, the component is positioned on the application fixture, and then fitted onto the application fixture along the application axis, such that liquid is supplied to the section that is to be wetted by means of the application fixture, and can then be removed by means of the suction device. The application fixture preferably has a first end and a second end, wherein The application fixture is designed to supply, at the first end, the liquid medium for application to the section of the component that is to be wetted, and The suction device is designed to generate a vacuum at the second end, in order to at least partially, create a vacuum between the region of the first end and the second end.

Because the liquid medium is applied to the section to be wetted by means of the application fixture in the region of the first end, and the suction device draws the applied liquid toward the second end of the application fixture, it is obtained, on one hand, that excess liquid is removed thereby from the component that is to be wetted. A further swabbing of the component to be wetted by means of a sponge disc, as has previously been the standard practice, is eliminated, such that in this manner the risk of contamination from particles introduced thereby is also prevented. Furthermore, as a result of the drawing of the liquid medium away from the first end of the application fixture towards the second end of the application fixture, the liquid medium is distributed over the section of the component that is to be wetted. The liquid medium flows, drawn by the suction device, along the component to be wetted from the first end of the application fixture to the second end of the application fixture, such that a film of liquid is applied to the section of the component that is to be wetted.

Not only is the excess liquid drawn off by means of the suction device, but vapors resulting from the evaporation of the liquid medium are also removed, such that an odor, disturbing for the user, is also substantially eliminated.

The device according to the invention can be designed for the wetting of an interior wall of an opening on the component that is to be wetted and/or an exterior wall of said component. For this, a specifically designed application fixture is used in each case that is adapted to the design of the section of the component to be wetted, thereby enabling a selective wetting of an interior and/or exterior wall of a tube made, for example, of plastic. If a specific component is to be wetted, or if another section of a component (e.g. instead of an exterior wall of a tube end, and interior wall of a tube end) is to be wetted, then the application fixture is exchanged and another application fixture, accordingly adapted, is connected to the dispenser and used.

In a first concrete design, the application fixture can be designed as a spigot on which the component can be placed at its opening for a selective wetting of an interior wall of the component. The component, which is designed as a tube, for example, is placed with its opening on the tap that forms the application fixture in such a manner that the tap in its applied state forms a contact with the section of the interior wall of the component that is to be wetted at least at the points of contact, and can wet the component on the interior wall of the opening.

In other designs, the application fixture may also be designed as a sleeve, into which the component can be inserted with the section to be wetted for a selective wetting of an exterior wall of the component. By way of example, a tube is inserted at the end in the application fixture having the form of a sleeve, such that the application fixture having the form of a sleeve lies flat on the section of the exterior wall of the tube that is to be wetted, when the tube is in the inserted state.

If both an interior and exterior wall of an opening, e.g. a tube end, are to be wetted simultaneously, then, in another design, the dispenser may have two application fixtures, of which a first application fixture is designed as a tap, and a second application fixture is designed as a sleeve encompassing said tap. For the wetting, the component is inserted between the tap and the sleeve such that the component, e.g. a tube end, is slid over the tap with its opening, and at the same time inserted into the sleeve. In this manner, both the interior wall and exterior wall of an opening of a component can be wetted simultaneously by means of the first application fixture and the second application fixture.

In a concrete embodiment, the application fixture can include a channel for supplying the liquid medium to the region of the first end of the application fixture. For this, the application fixture has a groove in the wall which faces the section of the component to be wetted when the component is fitted to the application fixture, which is in a flow connection with the channel, and runs at least in part along the circumference of the wall aligned with the application axis.

This groove may be circular in shape and run along the wall of the application fixture extending along the application axis. The liquid medium is then applied by means of the groove to the component that is to be wetted in the region of the first end of the application fixture in a circular fashion. Because the liquid medium is drawn by the suction device from the first end to the second end of the application fixture, the liquid medium is distributed on the component, and a liquid film is applied to the section of the component to be wetted, wherein simultaneously, excess liquid is drawn off and removed by means of the suction device.

The wetting procedure can be automatically executed for the most part by means of the device. For wetting, the component is fitted with its section that is to be wetted on the dispenser, and the liquid medium is applied to the section of the component that is to be wetted by means of the dispenser. Excess liquid is then removed by means of the suction device, while at the same time the liquid is distributed on the section of the component that is to be wetted such that in a desired manner, a liquid film results on the section to be wetted. For this, the operation of the device is simple and substantially independent of the user.

In order to further automatically control the application of the liquid medium, a dosage device may be provided, designed such that the liquid medium is dosed in relation to the surface area and shape of the section of the component to be wetted, such that for each wetting procedure, not too much, but also not too little, of the liquid is supplied and applied to the section of the component to be wetted.

The objective is furthermore achieved by means of a method for wetting a component with a liquid medium. With the method, it is provided that The component is fitted with a section to be wetted on a dispenser of a device for wetting the component, and The liquid medium is applied by the dispenser to the section to be wetted.

In addition, it is provided that at least a portion of the liquid medium is drawn off of the section of the component to be wetted by means of a suction device that is a part of the device for wetting the component.

The designs for the device described above can also be used for the method. In a similar manner, the advantages described also apply to the method according to the invention.

The method can be advantageously implemented for wetting a medical equipment component such as a tube or similar item, but can also be used fundamentally to wet any other component.

The dispenser used in the framework of the method can have at least one application fixture in an advantageous design, on which the component is fitted, and having a first end and a second end. In a first step, the liquid medium is supplied for application to the section of the component to be wetted by means of the first end, and in a second step, a vacuum is generated at the second end by means of a suction device, to, at least partially, draw off excess liquid from the region of the first end to the second end. As described above, in this manner, on one hand, an excess of liquid can be drawn off and thereby removed from the component after application, in order to prevent blockage in the opening of the component. In addition, by means of the suction device and the drawing of the liquid from the first end of the application fixture to the second end of the application fixture, the liquid medium is distributed along the section of the component to be wetted, thereby applying a liquid film to the section to be wetted. The suction device acts, on one hand, to remove the excess liquid, and on the other hand, ensures an even application of the liquid to the section of the component to be wetted. In addition, resulting vapors of the liquid can be disposed of by means of the suction device, thus preventing an odor from developing that is excessively disturbing for an operator.

The suction device draws off the liquid medium in that it creates a vacuum in the region of the second end of the application fixture. This vacuum is preferably generated for only a short period of time by means of a vacuum pulse, e.g. for a time period amounting to milliseconds or seconds. The wetting of the component takes place quickly thereby, in that immediately after the component has been attached to the dispenser, the liquid medium is applied, and then drawn off by means of the suction device. The total duration of the wetting procedure can last for significantly less than one second, preferably less than 500 ms, but can also last longer.

The application of the liquid medium by means of the application fixture and the removal of the liquid medium by means of the suction device can take place successively, or simultaneously.

In a first variation of the method, the liquid medium is first applied to the attached component by means of the application fixture at the first end of the application fixture, in order that subsequently, in a second step, the liquid medium is drawn towards the second end of the application fixture by means of the suction device, thereby distributing the liquid over the section of the component to be wetted and drawing off excess liquid.

In a second variation of the method however, the application of the liquid by means of the application fixture at the first end of the application fixture can take place simultaneously with the drawing off of the liquid. In supplying the liquid medium by means of the application fixture to the section of the component that is to be wetted, the suction device already generates a vacuum in this variation, such that the liquid supplied thereto is drawn directly towards the second end of the application fixture and thereby distributed along the section of the component that is to be wetted.

The basic idea of the invention shall be explained in greater detail below, based on the figures. They show.

Figure 1:
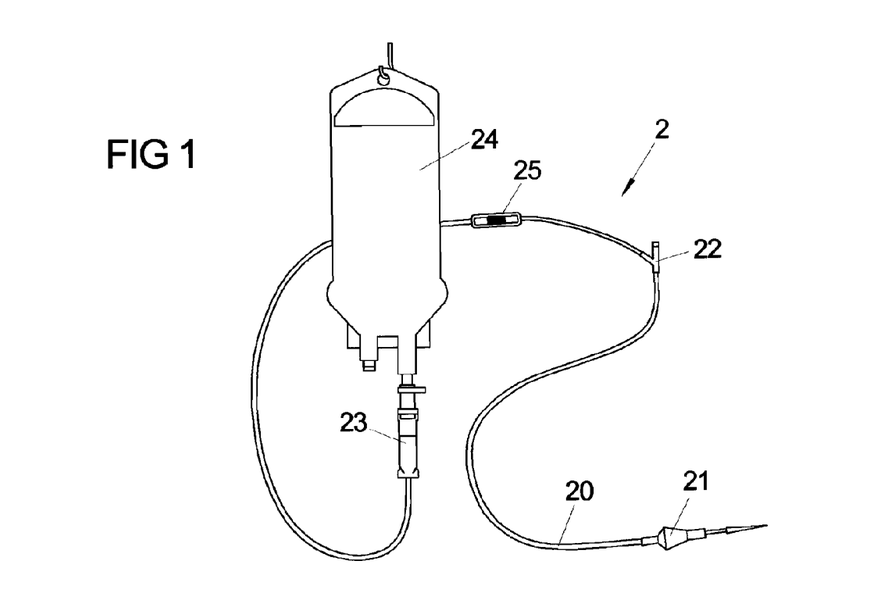
FIG. 1 A schematic representation of an infusion set.

FIG. 1 shows in a schematic overview, a medical equipment apparatus in the form of an infusion set 2, in which an infusion bag 24 (containing an infusion liquid, e.g. a medicine that is to be administered to a patient) is connected by means of a tube 20 made of plastic, in particular PVC, to a connector 21. The tube 20 can be connected to a port of an infusion cannula by means of the connector 21, in order to administer the liquid contained in the infusion bag 24 to a patient.

In the flow path between the bag 24 and the connector 21, in addition to the tube 20, there are a drip chamber 23, an actuating device 25 and a branch connection 22. The drip chamber 23 is disposed on an outlet opening of the bag 24 and connected to the tube 20. The actuating device 25 (e.g. in the form of a mechanical slider with which the tube 20 can be selectively opened or clamped off and thereby closed) is fitted on or slid onto the tube 20. The branch connection 22 connects two sections of the tube 20 with one another and serves as a connection for an additional bag in the infusion set 2.

To produce the infusion set 2, the individual components 20, 21, 22, 23, 25 must be connected to one another by the manufacturer (usually the bag 24 is first connected to the drip chamber 23 where a patient is to be administered to in that, for example, the drip chamber 23 is inserted by means of a tapered tap in the known manner in an accordingly designed output opening of the bag 24). In particular, a conventional adhesive connection is used for the connection of the tube 20 to the connector 21 at one end, and to the drip chamber 23 at the other end, which is created in that one end of the tube 20 is wetted with a liquid adhesive and attached to the connector 21 or drip chamber 23 respectively.

Figure 2:
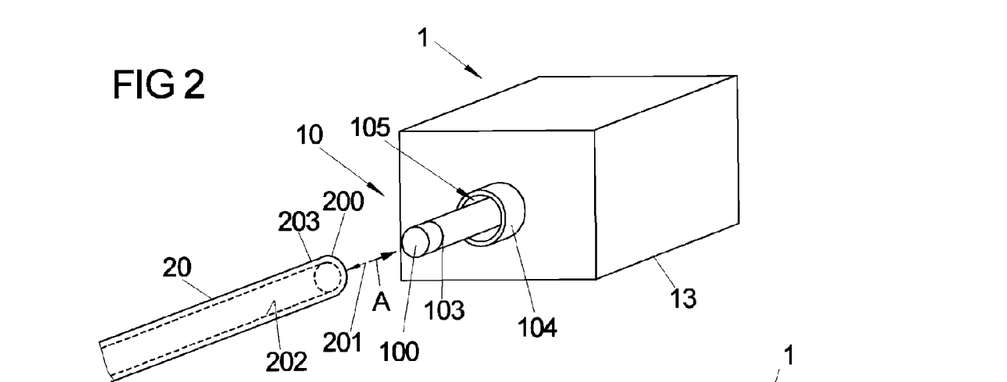
FIG. 2 A schematic, perspective view of a device for wetting a medical equipment component, in this case a tube of an infusion set.
Figure 3:
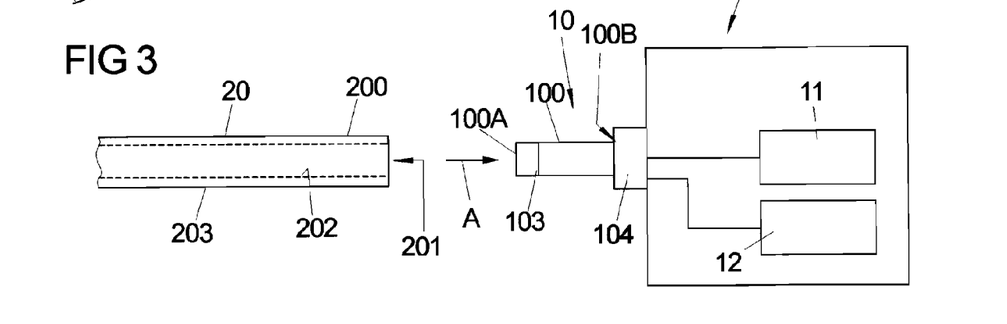
FIG. 3 Another schematic view of the device for wetting a medical equipment component.

To wet a component of a medical equipment apparatus, such as the tube 20 of the infusion set 2, the present invention envisions a device 1 such as that schematically depicted in FIGS. 2 and 3 as an embodiment example. The device 1 contains a dispenser 10 disposed on a housing 13 of the device 1 and serves for the application of a liquid medium on a section 200 of the tube 20 that forms a medical equipment component that is to be wetted. The device 1 contains a dosage device 11 for the automatic dosing of the quantity of the liquid medium that is to be applied in a wetting procedure, and a suction device 12 for drawing off at least a portion of the liquid medium from the section 200 of the tube 20 that is to be wetted.

Figure 4:
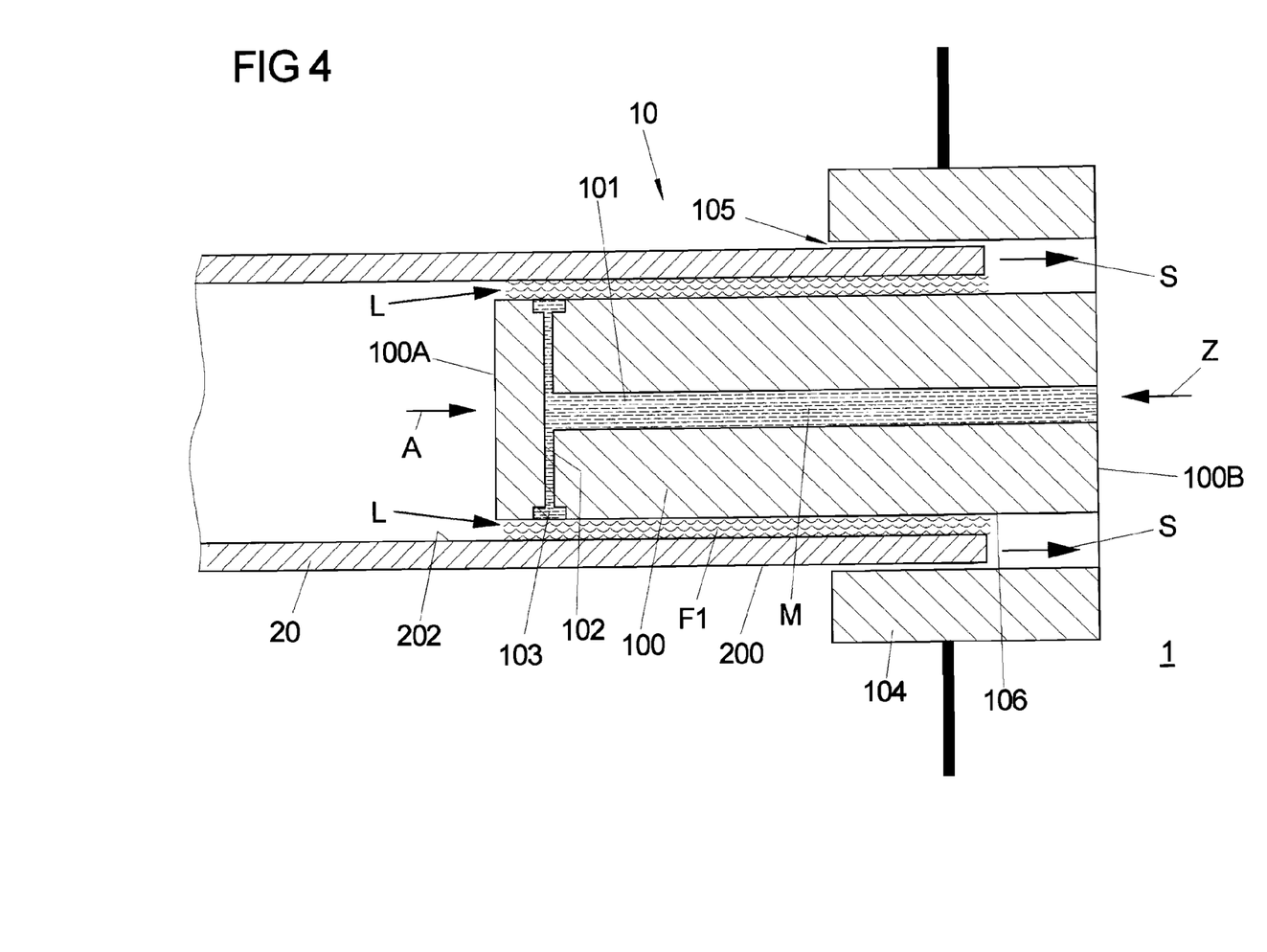
FIG. 4 A schematic view of a first concrete design of a dispenser for the device.

The dispenser 10 has an application fixture 100 in the depicted embodiment example in the form of spigot, as is depicted in detail in FIG. 4. The application fixture 100 in the form of a spigot extends along an application axis A, along which the tube 20 in the form of the tube that is to be fitted onto the application fixture 100, away from the housing 13 of the device 1. In this case, the spigot-like application fixture 100 is designed as a circular cylinder corresponding to the shape of an interior opening 201 of the tube 20, and is encompassed by a retaining ring 104 having a radial spacing to said, at least at the end 100b facing the housing 13. An intake opening 105 is formed between the retaining ring 104 and the spigot-like application fixture 100, in which the tube 20 can be inserted with the opening 201.

For wetting, the tube 20 is slid onto the application fixture 100 at the section 200 that is to be wetted (disposed at the end of the tube), such that the application fixture 100 is inserted into the opening 201, thus forming contact with the interior wall 202 of the tube 20. The tube 20 is held in place in this instance in the receiving opening 105 between the application fixture 100 and the cylindrical retaining ring 104, which encompasses the application fixture 100 in a ring-like manner.

As is apparent from the schematic depiction in accordance with FIG. 4, the application fixture 100 in the form of the cylindrical spigot has an interior channel 101 which extends along the application axis A in the application fixture 100. This channel 101 is connected in the flow path, by means of another channel 102 running at a right angle to the application axis A, to a groove 103, disposed on a first end 100A of the application fixture 100 facing away from the housing 13, running in a circular fashion along the cylindrical sheathing shaped outer wall 106 of the spigot-like application fixture 100.

In the framework of the wetting procedure, the tube 20 is first inserted in the receiving opening 105 with its section 200 that is to be wetted, and thereby inserting the application fixture 100 into the opening 201 of the tube 20. By means of the dosage device 11 (see FIG. 3), a predetermined dose of the liquid medium M is supplied via the channels 101, 102 along a intake axis Z to the first end 100A of the application fixture 100 and applied via the groove 103 in a circular fashion to the interior wall 202 of the tube 20.

Simultaneously with this fitting or following the fitting, a vacuum is generated by means of the suction device 12 (see FIG. 3) in the region of a second end 100B of the application fixture 100 facing the housing 13, in the space of the receiving opening 105 between the application fixture 100 and the retaining ring 104, by means of which, the liquid M applied to the interior wall 202 of the tube 20 in the region of the first end 100A of the application fixture 100 is drawn along a vacuum axis S to the second end 100B of the application fixture 100, such that the liquid medium M flows along the interior wall 202 of the tube 20 thereby forming a liquid film F1 on the interior wall 202 of the tube 20.

By the drawing of the liquid medium M via the suction device 12, firstly, the excess liquid M is drawn off and removed. As a result, the risk of a blockage to the tube 20 by means of the liquid medium M due to capillary effects is substantially eliminated.

Secondly, the liquid M is simultaneously distributed onto the interior wall 202 in the region of the section to be wetted, forming a liquid film F1, such that it is ensured that the tube 20 is evenly coated with a liquid film F1 in the region of the section 200 along the desired segment.

In addition, as a result of the drawing of the liquid medium M, the risk of contamination of the liquid film F1 is at least reduced. This is because, as a result of the drawing of the liquid medium M towards the second end 100B of the application fixture 100, a subsequent airflow L is drawn in the region of the first end 100A of the application fixture 100, which flows together with the liquid M to create a flow-through between the interior wall 202 of the tube 20 and the application fixture 100 to the second end 102B of the application fixture 100, removing any particles from this region that may be present.

The vacuum generated by the suction device 12 is preferably applied for only a short period of time in the manner of a vacuum pulse, lasting a few milliseconds (e.g. 100 milliseconds) or seconds. This vacuum pulse can be applied simultaneously with the introduction of the liquid M in the intake axis Z via the channels 101, 102 or after the introduction. On the whole, this results in a very short wetting procedure that can be completed in less than a second, e.g. less than 0.5 seconds.

The nature of the liquid film, in particular the quantity of the liquid M contained in the liquid film F1, and the thereby resulting thickness of the liquid film F1, can be adjusted by means of the dosage volume via the dose device 11 and the vacuum period and the vacuum obtained by the suction device 12.

After a successful wetting procedure, the end 200 of the tube 20 is removed from the dispenser 10 and connected at the wetted section 200 to the component to which it is to be connected, e.g. the connector 21 (see FIG. 1), in order to connect said to the tube 20 in an adhesive manner.

Figure 5:
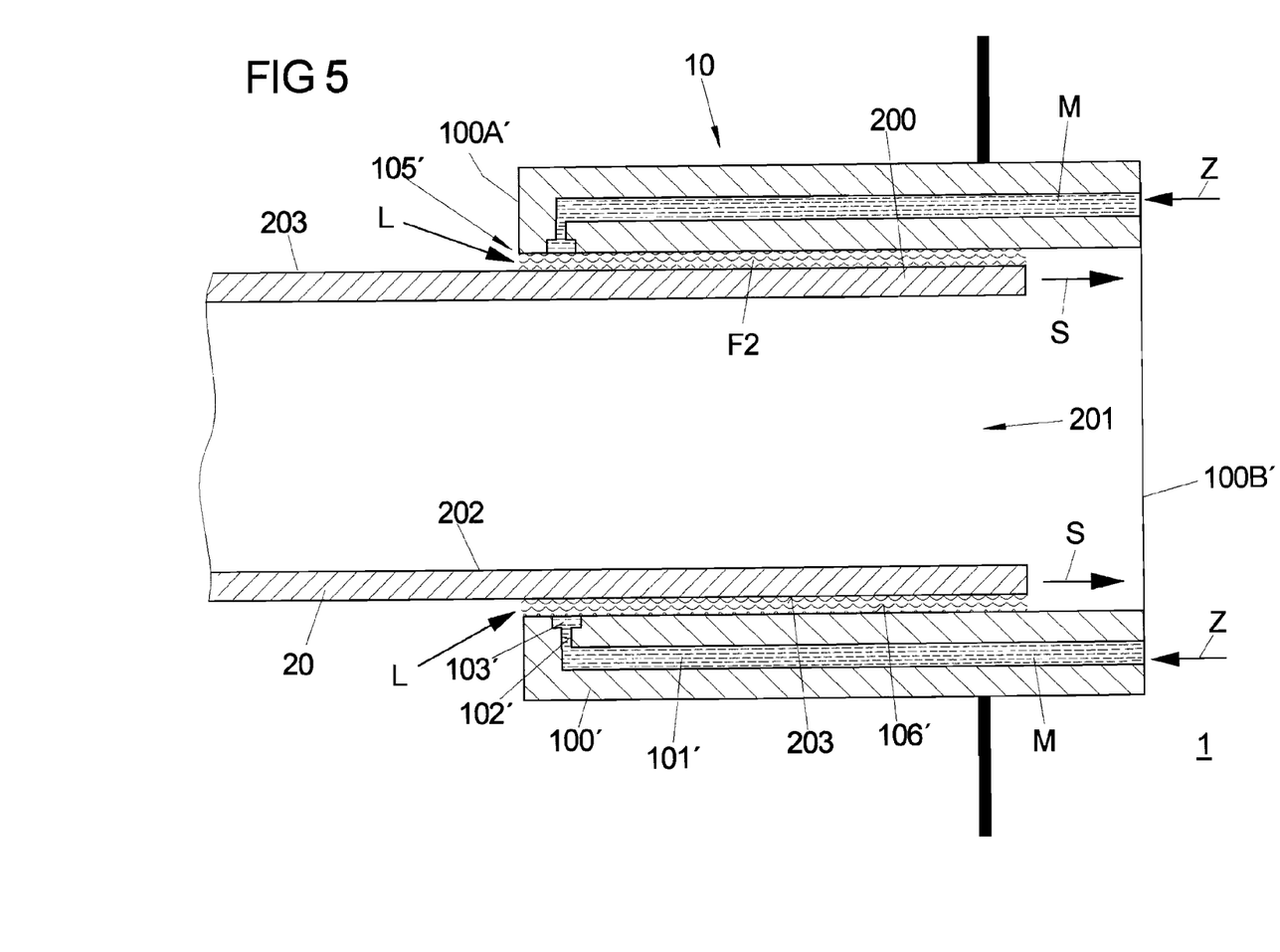
FIG. 5 A schematic view of a second concrete design of a dispenser for the device.

With an embodiment example depicted schematically in FIG. 5, the dispenser 10 has an application fixture 100' in the form of a sleeve, which is designed as a circular cylinder in its shape, and having a receiving opening 105' in which the section 200 of the tube 20 that is to be wetted is inserted. The application fixture 100' furthermore contains a channel 101' or numerous channels 101' connected in the flow path via one or numerous channels 102' to a circular groove 103' forming a ring running along the circumference on the interior wall 106' of the sleeve-shaped application fixture 100'.

The application fixture 100' serves to wet the exterior wall 203 of the tube 20 in the region of its tube end. For this, the end of the tube 20 is inserted in the receiving opening 105' of the application fixture 100', and the liquid M is guided by means of the channels 101', 102' towards a first end 100A' of the application fixture 100' and applied by means of the ring shaped groove 103' to the exterior wall 203 of the tube 20. Then, simultaneously with the application or subsequently after the application, a vacuum is generated by the suction device 12 (see FIG. 3) of the device 1 in the region of a second end 100B' of the application fixture 100', in order to, in this manner, draw the liquid M applied in the region of the first end 100A' on the exterior wall 203 of the tube to the second end 100B' of the application fixture 100', and by this manner generate a liquid film F2 on the exterior wall 203 of the tube 20 and draw off excess liquid M.

In order to generate an effective vacuum in the region of the second end 100B' of the application fixture 100', an additional central spigot may provided, disposed within the receiving opening 105' with a radial separation from the interior wall 106' of the application fixture 100', fixed in a permanent manner to the application fixture 100', which engages in the opening 201 of the tube 20 when said tube 20 is inserted therein.

Figure 6:
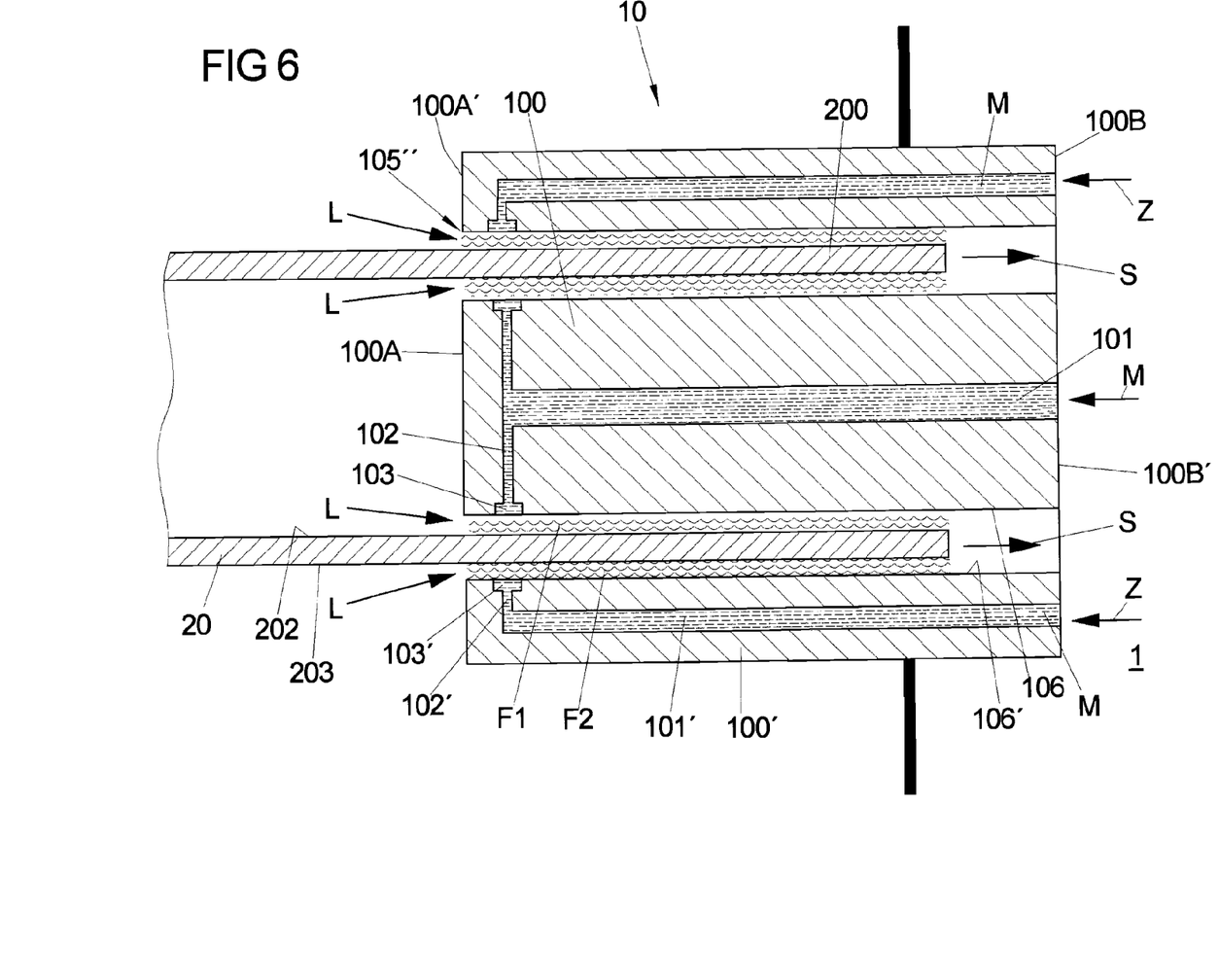
FIG. 6 A schematic view of a third concrete design of a dispenser for the device.

In another embodiment example depicted in FIG. 6, both an application fixture 100 according to the type having an inner spigot, as well as an application fixture 100' according to the type having a sleeve, are provided. By means of the two application fixtures 100, 100', both a liquid film F1 on the interior wall 202 as well as a liquid film F2 on the exterior wall 203 of the tube 20 can be applied in order to wet the tube at its end on both the interior and exterior. The wetting procedure for this is analogous to those described above, such that reference should be made to the explanations above.

In order to be able to wet different medical equipment components, e.g. tubes 20 of different types, e.g. having different diameters, different application fixtures 100, 100' having different concrete shapes may be used, wherein a specific application fixture 100, 100' is adapted to the geometric shape of the component that is to be wetted. If different components are to be wetted with the same device 1, the dispenser 10 is equipped with an appropriate application fixture 100, 100' depending on the respective component that is to be wetted, wherein, advantageously, the application fixture 100, 100' is releasable, and can be exchanged, in order to be able to wet other components is subsequent work procedures.

The device 1 can be created in such a manner, and designed such that the wetting procedure can be automatically initiated at the moment that the component to be wetted is attached to the dispenser 10. For this, an appropriate detection device may be provided, which recognizes whether a component is correctly attached to the dispenser 10, in order to subsequently execute the wetting procedure by applying the liquid M by means of the dosage device 11 and drawing said by means of the suction device 12.

The basic idea of the invention is not limited to the embodiment examples portrayed above, but rather can also be realized with embodiments of fundamentally different types. In particular, different medical equipment components can be wetted in the manner described herein by means of the device described herein in order to coat said with a liquid film in this manner. The invention is not limited to the wetting of tubes for use in an infusion set.

In addition, the invention is not limited to the wetting with a liquid medium for the purpose of establishing an adhesive attachment of one component to another. A device of the type portrayed herein can also be used, as a rule, to apply a liquid medium in the form of a lubricant, e.g. isopropanol, to facilitate the connection of two components, or in the form of a medical silicone for siliconizing a component. Other application possibilities in which a liquid film is to be applied to a medical equipment component, are also conceivable.

REFERENCE SYMBOL LIST

1 Device
10 Dispenser
100, 100' Application fixture
100A, 100B, 100A', 100B' End
101, 102, 101', 102' Channel
103, 103' Encircling groove
104 Retaining ring
105, 105', 105" Receiving opening
106, 106' Wall
11 Dosage device
12 Suction device
13 Housing
2 Infusion set
20 Component (tube)
200 Section to be wetted
201 Opening
202 Interior wall
203 Exterior wall
21 Connector
22 Branch connection
23 Drip chamber
24 Infusion bag
25 Actuating device
A Application axis
F1, F2 Liquid film
L Airflow
M Liquid
S Vacuum axis
Z Intake axis

The invention claimed is:

1. A device for wetting a section of a medical component with a liquid medium, the device comprising a dispenser for the application of the liquid medium, the dispenser comprising:
an application fixture configured to receive the section of the medical component to be wetted, the application fixture having a proximal end and a distal end,
an elongated wall extending from the distal end to the proximal end of the application fixture, the elongated wall having an opening spaced from the distal end of the application fixture through which the liquid medium is provided to the medical component to be wetted, and
a channel extending therethrough from the proximal end to the opening of the elongated wall, the channel configured to provide the liquid medium to the section of the medical component via the opening of the elongated wall; and
a suction device disposed at the proximal end of the application fixture for drawing at least a portion of the liquid medium over the section of the component to be wetted and toward the proximal end of the application fixture.

2. The device of claim 1, wherein the application fixture is designed as a spigot or tap having an opening through which the liquid medium passes and is thereby selectively applied to a section of an interior wall of the medical component to be wetted.

3. The device of claim 1, wherein the application fixture includes a groove on the elongated wall facing the section of the medical component that is to be wetted, wherein the groove is in fluid communication with the channel via the opening.

4. The device of claim 3, wherein the application fixture is cylindrical and the groove is a circumferential ring formed within the elongated wall of the application fixture.

5. The device of claim 1, further comprising a dosage device for the automatic dosing of the quantity of the liquid medium that is to be supplied by means of the dispenser.

6. The device of claim 1, further comprising a housing, wherein the dispenser is disposed on the housing.

7. A device for wetting a section of a medical component with a liquid medium, the device comprising a dispenser for the application of the liquid medium, the dispenser comprising:
an application fixture configured to receive the section of the medical component to be wetted, the application fixture having a proximal end and a distal end,
an elongated wall extending from the distal end to the proximal end of the application fixture, the elongated wall having an opening spaced from the distal end of the application fixture through with the liquid medium is provided to the medical component to be wetted,
a channel extending therethrough from the proximal end to the opening of the elongated wall, the channel configured to provide the liquid medium to the section of the medical component via the opening of the elongated wall;
a retaining ring, wherein the retaining ring and a portion of the elongated wall together define a receiving opening configured to receive the section of the medical component to be wetted along an application axis and on a portion of the first end of the application fixture; and
a suction device disposed at the proximal end of the application fixture that draws air in a direction from the distal end toward the proximal end of the application fixture.

8. The device of claim 7, wherein the portion of the elongated wall is located on the distal end of the application fixture and the suction device draws air in a direction from the distal end toward the proximal end of the application fixture along a vacuum axis that extends parallel to the application axis.

9. The device of claim 1 wherein a portion of the channel extends in a direction substantially parallel to the elongate wall.

10. The device of claim 1 wherein a connecting conduit between the channel and the opening extends in a direction substantially perpendicular to the channel.

* * * * *